(12) United States Patent
Gelmont et al.

(10) Patent No.: US 9,988,332 B2
(45) Date of Patent: *Jun. 5, 2018

(54) PREPARATION OF BROMINE-CONTAINING AROMATIC COMPOUNDS AND THEIR APPLICATION AS FLAME RETARDANTS

(71) Applicant: BROMINE COMPOUNDS LTD., Beer Sheva (IL)

(72) Inventors: Mark Gelmont, Haifa (IL); Michael Yuzefovitch, Haifa (IL); David Yoffe, Haifa (IL); Ron Frim, Haifa (IL)

(73) Assignee: BROMINE COMPOUNDS LTD., Beer-Sheva (IL)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/284,596

(22) Filed: Oct. 4, 2016

(65) Prior Publication Data

US 2017/0022133 A1    Jan. 26, 2017

Related U.S. Application Data

(62) Division of application No. 14/759,174, filed as application No. PCT/IL2014/000002 on Jan. 6, 2014, now Pat. No. 9,481,621.

(60) Provisional application No. 61/749,330, filed on Jan. 6, 2013.

(51) Int. Cl.
| | |
|---|---|
| C07C 17/10 | (2006.01) |
| C07C 17/12 | (2006.01) |
| C07C 25/18 | (2006.01) |
| C07C 41/14 | (2006.01) |
| C07C 17/275 | (2006.01) |
| C09K 21/08 | (2006.01) |
| C07C 43/29 | (2006.01) |
| C08K 5/03 | (2006.01) |
| C08K 5/06 | (2006.01) |
| C08K 5/375 | (2006.01) |

(52) U.S. Cl.
CPC ............ *C07C 41/14* (2013.01); *C07C 17/275* (2013.01); *C07C 25/18* (2013.01); *C07C 43/29* (2013.01); *C08K 5/03* (2013.01); *C08K 5/06* (2013.01); *C08K 5/375* (2013.01); *C09K 21/08* (2013.01)

(58) Field of Classification Search
CPC .............................. C07C 25/18; C07C 17/275
USPC .......................................................... 570/184
See application file for complete search history.

(56) References Cited

U.S. PATENT DOCUMENTS

| | | | |
|---|---|---|---|
| 2,623,910 A * | 12/1952 | Robinson ............. | C07C 17/266 252/581 |
| 3,006,972 A * | 10/1961 | Fields ..................... | C07C 2/861 568/930 |
| 3,331,797 A | 7/1967 | Kopetz et al. | |
| 3,459,687 A * | 8/1969 | Bufton ..................... | B01J 39/20 521/29 |
| 3,658,634 A | 4/1972 | Yanagi et al. | |
| 3,821,320 A | 6/1974 | Mark et al. | |
| 3,962,164 A | 6/1976 | Praetzel et al. | |
| 4,376,837 A | 3/1983 | Jenkner et al. | |
| 4,525,513 A | 6/1985 | Hochberg et al. | |
| 5,003,117 A | 3/1991 | Hussain | |
| 6,028,156 A | 2/2000 | Peled et al. | |
| 6,063,852 A | 5/2000 | Hussain | |
| 7,601,774 B2 | 10/2009 | Kornberg et al. | |
| 9,481,621 B2 * | 11/2016 | Gelmont ................. | C07C 25/18 |
| 2007/0205403 A1 | 9/2007 | Kornberg et al. | |
| 2007/0257241 A1 | 11/2007 | Kornberg et al. | |

FOREIGN PATENT DOCUMENTS

| | | |
|---|---|---|
| DE | 26 36 027 | 2/1978 |
| DE | 33 20 333 | 1/1984 |
| EP | 0 047 866 | 3/1982 |
| EP | 0 481 126 | 4/1992 |
| JP | 47-32298 | 8/1972 |
| JP | 56-5784 | 2/1981 |
| JP | 2008-506829 | 3/2008 |
| WO | WO 2006/013554 | 2/2006 |
| WO | WO 2012/127463 | 9/2012 |
| WO | WO 2013/054325 | 4/2013 |
| WO | WO 2014/061010 | 4/2014 |

OTHER PUBLICATIONS

Chinese Office Action issued in Appln. No. 201480004078.9 dated Apr. 19, 2017 (w/ translation).
Ross et al., "Some Reactions of Pentachlorobenzyl Chloride and Pentachlorobenzal Chloride; Steric Hindrance in the Alcoholysis of Pentachlorobenzal Chloride," *JACS*, vol. 71: 2756-2758 (Aug. 31, 1949).
"Emerging "new" Brominated Flame Retardants in Flame retarded Products and the environment", Norwegian Pollution Control Authority, 2462, 2009, pp. 1-114, Dec. 31, 2009, .pp. 39, 46, 47, 100.
"Scientific Opinion on Emerging and Novel Abrominated Flame Retardants in Food", EFSA Panel on Contaminants in the Food Chain EFSA Journal 2012 10 (10); 2908 pp. 1-333 Oct. 31, 2012, 29, 94.

(Continued)

*Primary Examiner* — Brieann R Johnston
(74) *Attorney, Agent, or Firm* — Nixon & Vanderhye P.C.

(57) ABSTRACT

The invention relates to compounds of the formula Ar(—$CH_2C_6Br_5$)$_y$, wherein Ar indicates a structure comprising one or more six-membered aromatic ring(s) and —$CH_2C_6Br_5$ indicates a pentabromobenzyl group, characterized in that at least one carbon atom of said six-membered aromatic ring(s) is bonded to the benzylic carbon of said —$CH_2C_6Br_5$ group, wherein y, which indicates the number of the —$CH_2C_6Br_5$ groups in said compound, is not less than 1. Processes for preparing the compounds and their use as flame retardants are also disclosed.

8 Claims, No Drawings

(56) References Cited

OTHER PUBLICATIONS

CAPlus Abstract of JP 47032298 (AN 1973:98932, May 1984, 1 page).
Extended European Search Report issued in App. No. 14735115.9 dated Aug. 2, 2016.
International Search Report for PCT/IL2014/000002, dated Apr. 2, 2014, 4 pages.
International Search Report issued in PCT/IL2015/050700 dated Oct. 26, 2015.
Written Opinion of the ISA for PCT/IL2014/000002, dated Apr. 2, 2014, 6 pages.
Burkhardt et al., Flameproofing agents based on tetrabromoxylene *Chemiker-Zeitung*, vol. 102, No. 1: pp. 11-18 (1978).
Lockner et al., "Practical Radical Cyclizations with Arylboronic Acids and Trifluoroborates" *Organic Letters Author manuscript* [online] vol. 13, No. 20: pp. 5628-5631 (Oct. 21, 2012).
Rueda-Zubiaurre et al., "Rational Design of a Nonbasic Molecular Receptor for Selective $NH_4^+/K^+$ Complexion in the Gas Phase" *Chemistry—A European Journal*, vol. 18, No. 52: pp. 16884-16889 (2012).
Japanese Office Action issued in Appln. No. 2015-551249 dated Dec. 5, 2017 (w/ translation).

\* cited by examiner

PREPARATION OF BROMINE-CONTAINING AROMATIC COMPOUNDS AND THEIR APPLICATION AS FLAME RETARDANTS

This application is a divisional of U.S. application Ser. No. 14/759,174 filed Jul. 2, 2015, which is a national phase of International Application No. PCT/IL2014/000002 filed Jan. 6, 2014, which claims the benefit of U.S. Provisional Application No. 61/749,330 filed Jan. 6, 2013, the entire contents of each of which are hereby incorporated by reference.

The present invention provides a novel class of pentabromobenzyl moiety-containing aromatic compounds having high molecular weight, which are suitable for use as flame retardants in polymers (e.g., polyamide, polypropylene and acrylonitrile-butadiene-styrene compositions).

Brominated compounds are known to be highly effective as flame retardants, and in many cases they constitute the only viable option for reducing the fire risk of synthetic materials. There exists a need to develop new, high molecular weight, macro-molecular brominated flame retardants. It is postulated that the higher the molecular weight of the brominated flame retardant, the lower is its volatility and its ability to bio-accumulate in living tissues.

Low molecular weight compounds containing a pentabromobenzyl moiety are known in the art. Pentabromobenzyl acrylate (EP 481126), pentabromobenzyl terephthalate (DE 33 20 333) and pentabromobenzyl tetrabromophthalate (EP 47866) have been reported to be useful in flame retarded polymer compositions. Furthermore, poly (pentabromobenzyl acrylate) is used as a flame retardant agent in flammable materials. Hereinafter, the pentabromobenzyl group is sometimes described by means of its molecular structure:

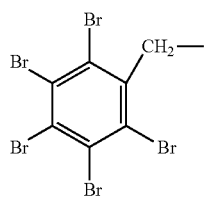

or its molecular formula —$CH_2C_6Br_5$.

The present invention provides novel compounds containing a pentabromobenzyl moiety and possessing highly satisfactory flame retarding properties. These compounds are prepared using electrophilic C-alkylation of different aromatic compounds with pentabromobenzyl halide, in particular bromide, in the presence of Friedel-Crafts catalysts. The pentabromobenzyl group-containing compounds of the invention have high molecular weight (>1000), their bromine content is preferably not less than 70%, they are insoluble in water and are also stable against hydrolysis and/or decomposition.

The compound of the invention has the formula $Ar(—CH_2C_6Br_5)_y$, wherein Ar indicates a structure comprising one or more six-membered aromatic ring(s), characterized in that at least one carbon atom of said six membered aromatic ring(s) is bonded to the benzylic carbon of a —$CH_2C_6Br_5$ group, wherein y, which indicates the number of the —$CH_2C_6Br_5$ groups in the compound of the invention, is not less than 1.

Preferably, Ar contains one six-membered aromatic ring, or two, preferably non-fused, six-membered aromatic rings, and y is at least equal to twice the number of the six-membered aromatic rings in Ar. It should be noted that each of the six membered aromatic ring(s) of which Ar is composed may be substituted, e.g., by alkyl group(s). When Ar consists of two six-membered aromatic rings, then these rings may be either connected by bridges selected from the group consisting of alkylene chains, —O— or —S—, or said rings may be fused together.

More specifically, the present invention provides a novel, aromatic, high weight macro-molecular compound which contains a plurality of pentabromobenzyl moieties, as shown by Formula (I), and/or a mixture of such compounds:

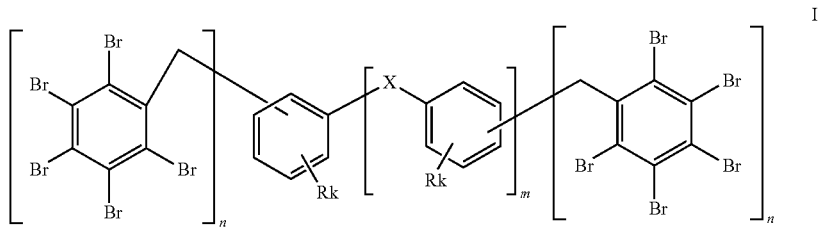

In formula (I), R is H or a linear or branched aliphatic chain, n is independently an integer from 1 to 3, preferably 2 or 3, m is 0 or 1, such that n+m·n equals y, k is an integer from 1 to 3, X=null, O, S, a linear or branched alkylene, e.g., an alkylene group containing 1 to 10 carbon atoms.

The compounds of the invention are prepared by reacting pentabromobenzyl halide, especially pentabromobenzyl bromide (chemically named 1-(bromomethyl)-2,3,4,5,6-pentabromobenzene and abbreviated herein PBBBr) with a starting material which comprises at least one six-membered aromatic ring, as set out above, in the presence of a suitable Friedel-Crafts catalyst (Lewis acids) such as $AlCl_3$, $AlBr_3$, $GaCl_3$, $FeCl_3$, $SnCl_4$, $SbCl_3$, $ZnCl_2$, $CuCl_2$ and HF, preferably $AlCl_3$. Thus, another aspect of the invention is a process comprising a Friedel-Crafts alkylation reaction of pentabromobenzyl halide with a reactant which contains one or more six-membered aromatic rings, in the presence of a Friedel-Crafts catalyst. In the so-formed $Ar(CH_2C_6Br_5)_y$ product, there is at least one bond between a carbon atom of an aromatic ring and the benzylic carbon of the pentabromobenzyl group.

Regarding the pentabromobenzyl bromide starting material, it is commercially available and produced by ICL-IP or can be prepared by methods known in the art (e.g., U.S. Pat. No. 6,028,156 and U.S. Pat. No. 7,601,774), according to the route of synthesis involving the aromatic bromination of toluene, for example in halogenated solvent(s), using elemental bromine, in the presence of a Lewis acid catalyst, e.g. $AlCl_3$, to form pentabromotoluene (abbreviated herein 5-BT), which is then brominated at the benzylic carbon using elemental bromine and a radical source e.g. azobisizobutiro nitrile, as illustrated by the following scheme (see U.S. Pat. No. 7,601,774):

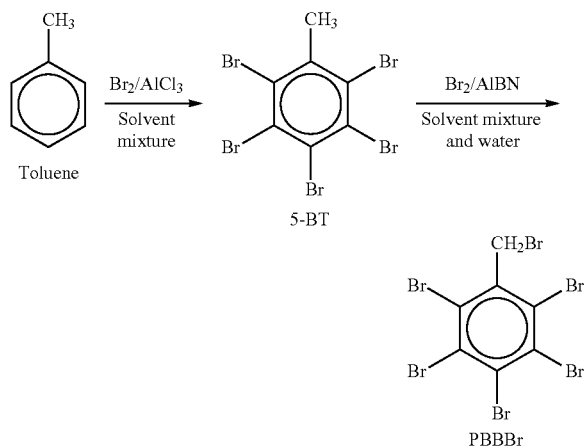

Regarding the starting material which undergoes aromatic substitution reaction, namely, electrophilic C-alkylation according to the invention, it contains one six-membered aromatic ring, or two, preferably non-fused, six-membered aromatic rings. Preferably, the reactant is represented by Formula (II):

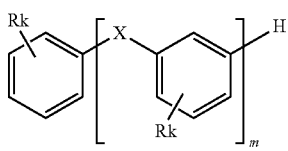

In formula (II) R is H or a linear or branched aliphatic chain, m is 0 or 1, k is an integer from 1 to 3, X=null, O, S, a linear or branched alkylene, e.g., an alkylene group containing 1 to 10 carbon atoms.

Exemplary starting materials of Formula II include:
Toluene, wherein R=$CH_3$, k=1, m=0;
Xylene, wherein R=$CH_3$, k=2, m=0;
Ethylbenzene, wherein R=$C_2H_5$, k=1, m=0;
Diphenyl ether, wherein R=H, X=O, m=1;
Diphenylmethane, wherein R=H, X=$CH_2$, m=1; and Diphenylethane, wherein R=H, X=$(CH_2)_2$, m=1;

The Friedel-Crafts alkylation reaction according to the invention is generally carried out in a solvent or a mixture of solvents, e.g., in halogenated aliphatic hydrocarbon which is preferably selected from the group consisting of dichloromethane, dibromomethane (DBM), bromochloromethane and dichloroethane (DCE). The molar ratio between the two reactants is suitably adjusted to satisfy the desired degree of substitution on the six membered aromatic ring(s). In general, it is desired to attach not less than two, and preferably three, —$CH_2C_6Br_5$ groups to each six-membered aromatic ring present in the starting material. The amount of the catalyst, e.g. $AlCl_3$, is preferably between 0.5% wt/wt and 2% wt/wt relative to PBBBr amount. The reaction is carried out under anhydrous conditions.

The reaction is generally carried out by combining the two reactants in the solvent under heating in order allow a complete dissolution of the PBBBr (and also of the second reactant, in the event that it is solid at room temperature), followed by the addition of the catalyst. The Friedel-Crafts alkylation reaction is accompanied by the generation of hydrogen bromide. The temperature of the reaction mixture is then increased, e.g., to 40° C.-90° C. and the reaction is allowed to reach completion. The product is virtually insoluble in the reaction medium, and precipitates almost instantly. In general, the reaction time is from 2 to 8 hours. The end of the reaction is indicated by the complete consumption of the PBBBr (its disappearance may be determined by gas chromatography analysis) or by the cessation of hydrogen bromide evolution.

Thus, the invention also relates to the use of pentabromobenzyl halide as an alkylation reagent in Friedel-Crafts alkylation of the reactants of Formula II. In a preferred embodiment, the invention provides a process comprising a Friedel-Crafts alkylation reaction of pentabromobenzyl halide, e.g., bromide, with a reactant selected from the group consisting of toluene, xylene, ethylbenzene, diphenyl ether, diphenylmethane and diphenylethane in the presence of aluminum chloride, wherein the molar ratio between said pentabromobenzyl bromide and said reactant is at least equal to twice the number of the six-membered aromatic rings of said reactant.

The product is isolated from the reaction mixture by means of conventional techniques. The reaction mixture is repeatedly washed with sodium bisulfite (SBS) solution and water, whereby the excess catalyst is destroyed. The solid is then separated from the liquid phase by filtration. The product can then be treated (slurried) in dichloromethane under heating for at least one hour, following which the slurry is cooled and the solid product is collected by filtration, and optionally washed and dried.

In general, the Friedel-Crafts alkylation of an aromatic compound with pentabromobenzyl bromide according to the invention leads to the formation of a product mixture consisting of several isomers and homologs [by homologs is meant the homologous series $Ar(CH_2C_6Br_5)_y$, in which y=1, 2, 3, and more up to 3+3m, wherein m+1 is the number of the six-membered rings in Ar]. The composition of the product mixture can be roughly determined on the basis of the percentage of bromine. Thus, the variable y, which indicates the number of pentabromobenzyl groups bonded to the six-membered aromatic ring(s), can be a non-integer number, indicating the average degree of pentabromobenzyl substitution of the product mixture. For example, Friedel-Crafts alkylation of toluene with pentabromobenzyl bromide can be controlled to give a product with high bromine content, e.g., of about 76%, which corresponds to a product mixture that can be identified by the formula $C_6H_{2.4}(CH_3)(CH_2C_6Br_5)_{2.6}$, indicating that the predominate homolog in the mixture is $C_6H_2(CH_3)(CH_2C_6Br_5)_3$, but that lower homologs, e.g., $C_6H_3(CH_3)(CH_2C_6Br_5)_2$, and possibly also $C_6H_4(CH_3)(CH_2C_6Br_5)$, are also present in the mixture. According to the simplified notation described in more detail below, the compound $C_6H_{2.4}(CH_3)(CH_2C_6Br_5)_{2.6}$ is named Tris(pentabromobenzyl) toluene. However, it should be noted that the experimental results reported below demonstrate that the resultant product mixture is useful as a flame retardant. In view of the fact that the reaction-derived product mixture exhibits said flame retardant properties, then there is no need to separate the mixture into its individual components. Similarly, there is no need to control the conditions of the reaction in order to favor one single desired component. By varying the reaction conditions, a product containing maximal pentabromobenzyl groups is obtained.

In one preferred class of the $Ar(CH_2C_6Br_5)_y$ compounds of the invention, Ar is toluene; this class of compounds is represented by Formula I, wherein m=0, R is $CH_3$ and k is 1, i.e., pentabromobenzyl-substituted toluene, especially Tris(pentabromobenzyl)toluene.

In another preferred class of the $Ar(CH_2C_6Br_5)_y$ compounds of the invention, Ar is selected from the group consisting of diphenylether, diphenylmethane and diphenylethane; this class of compounds is represented by Formula I, wherein m=1 and R is H. More specifically, this preferred class is also identified herein by Formula III:

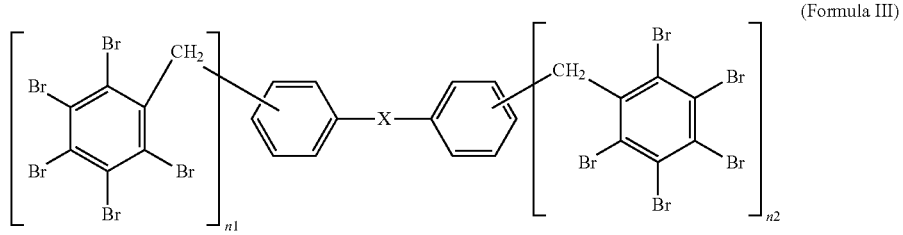

(Formula III)

wherein X is selected from the group consisting of —O—, —$CH_2$— and —$CH_2$—$CH_2$—, said compounds having bonds between carbon atoms of aromatic rings (of the diphenyloxide or diphenylalkane portion) and the benzylic carbon of —$CH_2C_6Br_5$ group, with n1 and n2 being independently 1, 2 or 3, and preferably 2 or 3, such that the bromine content of the compound is preferably not less than 60%, e.g., in the range from 60 to 78% by weight. More preferred are compounds of Formula III wherein X is —$CH_2$—$CH_2$—, having bromine content of not less than 70% by weight, e.g., in the range from 70 to 78% by weight. Especially preferred compounds of the invention are denoted herein pentakis(pentabromobenzyl)diphenylethane and hexakis(pentabromobenzyl)diphenylethane. As explained above, the product of Formula III consists in fact of a mixture of various —$CH_2C_6Br_5$ homologs. In the simplified notation used herein, a mixture is named according to the homolog which represents the average number of —$CH_2C_6Br_5$ group per molecule. For example, is the average number is 4.0, then the mixture is named tetrakis (pentabromobenzyl)diphenylethane. The average number of pentabromobenzyl groups per molecule would normally be a mixed number, in which case the average is rounded off via excess-rounding, i.e., to the next whole number. The term pentakis(pentabromobenzyl)diphenylethane therefore indicates a mixture consisting pentabromobenzyl-substituted diphenylethane molecules, having an average of between 4 and 5 pentabromobenzyl groups per molecule in the mixture (4<average≤5). Likewise, the term hexakis(pentabromobenzyl)diphenylethane indicates a mixture consisting of pentabromobenzyl-containing diphenylethane molecules, having an average of between 5 and 6 pentabromobenzyl groups per molecule in the mixture (5<average≤6). Thus, the notation used in naming the compounds of the invention is similar to the conventional notation applied in naming ar-brominated diphenyloxide and diphenylethane.

The compounds of the invention are useful as flame retardant agents in a flammable material. Accordingly, another aspect of the present invention is a flame-retarded formulation which comprises a flammable material (e.g., a polymer) and the novel compounds of the invention of the formula $Ar(CH_2C_6Br_5)_y$. Specifically, the compounds of the invention were tested in polyamides, polypropylene copolymers and acrylonitrile-butadiene-styrene and were found to demonstrate good activity.

The formulation of the invention comprises a flame-retarding effective amount of the novel $Ar(CH_2C_6Br_5)_y$ compounds of the invention, and especially the compounds of Formula I and III. The flammability characteristics of plastic materials are quantifiable according to the method specified by Underwriter Laboratories standard UL 94. The UL 94 ratings are V-0, V-1, and V-2. A material assigned with the V-0 rating is considered to be the less flammable.

A polymeric composition according to the invention which contains at least 5 wt %, and preferably 10 wt % bromine, would generally satisfy the UL 94 vertical burning test (the entire bromine content being supplied by the $Ar(CH_2C_6Br_5)_y$ compounds).

Other Conventional additives may also be included in the polymeric formulation. For example, an inorganic compound (typically a metal oxide) capable of cooperating with the novel $Ar(CH_2C_6Br_5)_y$ flame retardant for retarding the flammability of the polymer is preferably also present in the formulation. A preferred example of a suitable inorganic compound, which is generally considered as an "inorganic synergist", is antimony trioxide.

An exemplary polymer which can be flame-retarded with the novel $Ar(CH_2C_6Br_5)_y$ compounds of the invention include polyamide such as Nylon 66 [poly(hexamethylene adipamide]. Thus, another aspect of the invention is a flame-retarded formulation comprising polyamide and a flame retardant of the invention, especially a compound of Formula I or III, and in particular compounds selected from the group consisting of: pentakis(pentabromobenzyl)diphenylethane; and hexakis(pentabromobenzyl)diphenylethane.

The polyamide-based formulation comprises at least 30% polyamide, e.g., between 40% and 70% wt %. The polyamide formulation further comprises reinforcing fillers, namely, glass fibers, which are typically pre-coated by methods known in the art prior to their use in order to improve their compatibility with the polyamide matrix. Such modified forms of glass fibers are available in the market, e.g., GF Chop Vantage 3660 from PPG. The glass fibers comprise filaments with diameter in the range from 2µ to 20µ, and are applied in the form of pieces with length in the range from 2 to 10 mm, e.g., from 3 to 4.5 mm. For example, the major constituents of glass fibers applied for reinforcing polyamide is alumino-borosilicates; such type of glass in known as E-glass. The concentration of the glass fibers is from 5% to 40% of the total weight of the polyamide composition.

In addition to the polyamide, the reinforcing fillers, the bromine-containing compound of the formula $Ar(CH_2C_6Br_5)_y$ and antimony trioxide, the polyamide formulation of this invention may further contain lubricants, antioxidants (e.g., of hindered phenol or phosphite type), pigments, UV stabilizers and heat stabilizers. The concentration of each of the conventional additives listed above is typically in the range between 0.05 and 10 wt %.

The polyamide compositions are produced by melt-mixing the components, e.g., in a co-kneader or twin screw extruder, wherein the mixing temperature is in the range from 200 to 300° C. For example, the polyamide, the bromine containing flame retardant of formula Ar(CH$_2$C$_6$Br$_5$)$_y$ and the conventional additives (with the exception of the glass fibers) are dry blended and the blend is fed to the extruder throat. The glass fibers are the last to be added, i.e., downstream.

The experimental results reported below indicate that the novel Ar(CH$_2$C$_6$Br$_5$)$_y$ compounds of the invention demonstrate good activity in reducing the flammability of polypropylene copolymers. Thus, another aspect of the invention is a flame-retarded formulation comprising a polypropylene copolymer or impact modified polypropylene and a flame retardant of the invention, especially a compound of Formula I or III, and in particular compounds selected from the group consisting of: pentakis(pentabromobenzyl)diphenylethane; and hexakis(pentabromobenzyl)diphenylethane.

The polypropylene formulation preferably comprises a polypropylene copolymer in an amount of not less than 50 wt % (relative to the total weight of the formulation), e.g., from 50 to 85 wt %. Suitable polypropylene impact copolymer which can be used in the present invention can be in the form of block copolymers comprising a first block (or phase), which is essentially the polypropylene homopolymer component and a second block (or phase), which is an ethylene-propylene copolymer component. A polypropylene impact copolymer is produced by means of sequential polymerization reactions under conditions known in the art. The first reaction produces the homopolymer component and the second reaction produces the copolymer component. Thus, the copolymer component is chemically incorporated within the matrix of the homopolymer component. Different grades of polypropylene impact copolymer in the form of block copolymers are commercially available (Carmel Olefins, Israel, under the name Capilene® SE 50E, TR 50 and SL 50). Impact modified polypropylene can be prepared by admixing a polypropylene homopolymer and a rubber.

The compounds of the invention can be used to reduce the flammability of either filler-free or filler-containing polypropylene-based formulations. When a filler, e.g., talc is used, then its concentration is preferably in the range from 10-20 wt % relative to the total amount of the formulation. Other additives which can be incorporated in the polypropylene formulation are as set out above, for example, antimony trioxide.

The novel Ar(CH$_2$C$_6$Br$_5$)$_y$ compounds of the invention also display good activity in reducing the flammability of acrylonitrile-butadiene-styrene (ABS). Thus, another aspect of the invention is a flame-retarded formulation comprising ABS and a flame retardant of the invention, especially a compound of Formula I or III, in particular compounds selected from the group consisting of: pentakis(pentabromobenzyl)diphenylethane; and hexakis(pentabromobenzyl)diphenylethane.

ABS compositions of the invention preferably comprise not less than 50 wt % ABS (relative to the total weight of the formulation), e.g., from 50 to 85 wt % ABS. The term ABS refers in the context of the present invention to copolymers and terpolymers that include the structural units corresponding to (optionally substituted) styrene, acrylonitrile and butadiene, regardless of the composition and method of production of said polymers. Characteristics and compositions of ABS are described, for example, in Encyclopedia of Polymer Science and Engineering, Volume 16, pages 72-74 (1985). ABS with MFI between 1 and 50 g/10 min (measured according to ISO 1133 at 220° C./10 kg) are used.

The ABS compositions according to the present invention also include one or more anti-dripping agents such as polytetrafluoroethylene (abbreviated PTFE) in a preferred amount between 0.025 and 0.4 wt %, more preferably between 0.025 and 0.3 wt %, and even more preferably between 0.05 and 0.2 wt %. PTFE is described, for example, in U.S. Pat. No. 6,503,988.

Other additives which can be incorporated in the ABS formulation are as set out above, for example, antimony trioxide. Notably, the compounds of the invention, especially the compounds of Formula III, and in particular pentakis(pentabromobenzyl)diphenylethane; and hexakis(pentabromobenzyl)diphenylethane, exhibit excellent utility in ABS even in the presence of a small amount of antimony trioxide, e.g., less than 1.8 wt % Sb$_2$O$_3$ relative to the total weight of the formulation. ABS formulation comprising a compound of Formula III, as identified above, and antimony trioxide, wherein the weight ratio between the compound of Formula III and antimony trioxide is above 5:1, and preferably above 7:1, forms another aspect of the invention.

The plastic formulations set forth above are readily prepared by methods known in the art. The various ingredients of the formulation are blended together, according to their respective amounts. The ingredients may be first dry blended using suitable mixing machines, such as Henschel mixer. The resulting mixture may then be processed and compounded to form homogeneous pellets, for example, by using a twin screw extruder. The pellets obtained are dried, and are suitable for feed to an article shaping process such as injection molding. Other blending and shaping techniques can also be applied. Articles molded from the polymer formulations form another aspect of the invention.

EXAMPLES

Example 1

Reaction of Toluene with PBBBr

DBM (200 ml), PBBBr (62.2 g, 0.11 mol) and toluene (3.7 g, 0.04 mol) were placed into a 500 ml flask fitted with a mechanical stirrer, thermometer, condenser and N$_2$ inlet. The mixture was heated to 70° C. until the PBBBr had dissolved. AlCl$_3$ (0.7 g, 0.005 mol) was added and the vigorous formation of HBr started. The mixture was heated at 80° C. for 6 hours until the PBBBr disappeared (by GC). The reaction mixture was washed three times with water (3×120 ml) and SBS (1.5 ml, ~28% aqueous solution) taking 20 minutes for each washing. After that, the solid was filtered out and re-slurried with DCM (2×200 ml) at 40° C., for one hour (each reslurry). The reaction mixture was cooled to 20° C. and the solid was filtered off and dried in an oven at 150° C. under reduced pressure for 24 hours, to give 42.7 g, corresponding to ~75% yield, based on PBBBr. According to elemental analysis, the content of bromine is about 76% (parabomb), corresponding to ~2.7 PBBBr molecules per molecule of toluene. The product of this example is represented by the formula C$_6$H$_{2.3}$(CH$_3$)(CH$_2$C$_6$Br$_5$)$_{2.7}$ and is named Tris(pentabromobenzyl)toluene.

Example 2

Reaction of Toluene with PBBBr

The procedure of Example 1 was repeated, but using PBBBr (56.6 g, 0.1 mol), toluene (4.6 g, 0.05 mol), AlCl$_3$ (2.8 g, 0.02 mol) and dichloroethane (200 ml) as the solvent. The weight of the product was 49.5 g, corresponding to ~86% yield, the content of bromine is about 75.0%.

Example 3

Reaction of Diphenyloxide with PBBBr

The procedure of Example 1 was repeated, but using PBBBr (169.8 g, 0.3 mol), diphenyloxide instead of toluene (8.5 g, 0.05 mol) and $AlCl_3$ (2.8 g, 0.02 mol). The weight of the product was 115.7 g, corresponding to ~75% yield, the content of bromine is about 78%.

Example 4

Reaction of Diphenylmethane with PBBBr

The procedure of Example 1 was repeated, but using PBBBr (68 g, 0.12 mol), diphenylmethane instead of toluene (3.3 g, 0.02 mol) and $AlCl_3$ (1.4 g, 0.01 mol). The weight of the product was 41.8 g, corresponding to ~68% yield, the content of bromine is about 77.4%.

Example 5

Reaction of Diphenylethane with PBBBr

The procedure of Example 1 was repeated, but using diphenylethane (3.65 g, 0.02 mol) instead of toluene. The weight of the product was 35.6 g, corresponding to ~63% yield, the content of bromine is about 77%.

Example 6

Reaction of Diphenylethane with PBBBr

The procedure of Example 5 was repeated, but using dichloroethane as a solvent. The weight of the product was 46.7 g, corresponding to ~83% yield, the content of bromine is about 77%. The product is hexakis(pentabromobenzyl)diphenylethane.

Example 7

Reaction of Diphenylethane with PBBBr

DCE (1600 ml), PBBBr (805.6 g, 1.42 mol) and diphenylethane (57.70 g, 0.317 mol) were placed into a 2000 ml glass reactor fitted with a mechanical stirrer, thermometer, condenser and $N_2$ inlet. The mixture was heated to 70° C. and $AlCl_3$ (4.5 g, 0.17 mol) was added portionwise during ~3 hours. Then the mixture was heated for an additional hour at 65-75° C. until the PBBBr disappeared (by GC). The reaction mixture was washed three times with water (3×1000 ml) at ~60° C. and SBS (20 ml, ~28% aqueous solution) taking 20 minutes for each washing. After that, the solid was filtered off at 40-50° C., washed with 200 ml DCE, and dried in an oven at 150° C. under reduced pressure for 20 hours, to give 738 g, corresponding to an ~98% yield. The content of bromine was ~75%. The product is pentakis(pentabromobenzyl)diphenylethane.

Examples 8 and 9 (of the Invention) and 10 (Comparative)

V-0 Rated Flame Retarded Formulations of Polyamide 66

The products of Examples 1 and 7 were tested as flame retardants (FR) in nylon compositions according to the procedure described below. A commercially available polymeric flame retardant, FR-803P, was also tested for the purpose of comparison.

Ingredients Used to Prepare the Compositions

The materials used for preparing the nylon compositions are tabulated in Table 1:

TABLE 1

| TRADE NAME (PRODUCER) | GENERAL INFORMATION | FUNCTION |
| --- | --- | --- |
| Aculon S 223D (DSM) | Polyamide 66 (contains nucleating agent, mold release agent & lubricant) | Plastic matrix |
| FR-803P (ICL-IP) | Brominated polystyrene | FR |
| Product of Example 1 | Tris(pentabromobenzyl)toluene | FR |
| Product of Example 7 | Pentakis(pentabromobenzyl) diphenylethane | FR |
| GF ChopVantage 3660 (PPG) | Glass fibers | Reinforcing filler |
| AO M-0112 (Kafrit) | Antimony trioxide masterbatch, 77%, universal grade. | FR-synergist |
| Acrawax C (Lonza) | Multifunctional, nitrogen-containing, hindered phenol | Antioxidant & heat stabilizer |
| Irganox B1171 (Ciba) | N,N' ethylene bisstearamide | Lubricant |
| Ca Stearate | Ca-stearate | Lubricant |

Preparation of the Compositions and Test Specimens

The compounding was performed in a twin-screw co-rotating extruder ZE25 with L/D=32 (Berstorff). PA 66 pellets (which were dried overnight at 80° C. in a vacuum oven), the flame retardant, Acrawax C, Irganox B1171 and Ca stearate were weighed on Sartorius semi-analytical scales with subsequent manual mixing in plastic bags. The blend was then fed via feeder N° 1. The glass fiber was fed in via feeder N° 3 to the 5th section of the extruder via a lateral feeder. The compounding conditions are presented in Table 2. The extruded strands were cooled in a water bath and pelletized. The obtained pellets were dried in a vacuum at 80° C. overnight.

TABLE 2

| PARAMETER | UNITS | Set values | Read values |
| --- | --- | --- | --- |
| Feeding zone temperature ($T_1$) | ° C. | | |
| $T_2$ | ° C. | 250 | 234-256 |
| $T_3$ | ° C. | 270 | 269-285 |
| $T_4$ | ° C. | 270 | 259-287 |
| $T_5$ | ° C. | 270 | 267-270 |
| $T_6$ | ° C. | 270 | 262-279 |
| $T_7$ (vent) | ° C. | 275 | 265-286 |
| $T_8$ | ° C. | 275 | 268-293 |
| $T_9$ | ° C. | 280 | 264-281 |
| Temperature of melt | ° C. | | 260-281 |
| Screw speed | RPM | | 300 |
| Feeding rate | Kg/h | | 12 |

The dried pellets were injection molded into 1.6 thick test specimens using Allrounder 500-150 from Arburg. The conditions of the injection molding are tabulated in Table 3 below:

TABLE 3

| PARAMETER | UNITS | Set values |
|---|---|---|
| $T_1$ (Feeding zone) | °C. | 240 |
| $T_2$ | °C. | 260 |
| $T_3$ | °C. | 285 |
| $T_4$ | °C. | 290 |
| $T_5$ (nozzle) | °C. | 295 |
| Mold temperature | °C. | 90 |
| Injection pressure | bar | 1300 |
| Holding pressure | bar | 700-900 |
| Back pressure | bar | 10 |
| Injection time | sec | 40 |
| Holding time | sec | 6 |
| Cooling time | sec | 1 |
| Injection speed | ccm/sec | 50 |

The specimens were conditioned for at least 48 hours at 23° C., and were then subjected to the tests outlined below.

Tests

Flammability Test

The flammability test was carried out according to the Underwriters-Laboratories standard UL 94, applying the vertical burn on specimens of 1.6 mm thickness.

Mechanical Properties

Impact strength was measured using the Izod notched test according to ASTM D-256, using pendulum impact tester type 5102 (Zwick); Tensile properties (tensile strength, tensile modulus, elongation at yield and elongation at break) were measured in Zwick/Roell Z010 material testing machine according to ASTM D-638 (type 2 dumbbells were used, with the speed of test being 5 mm/min).

Thermal Properties

HDT (heat distortion temperature; this is the temperature at which a polymer sample deforms under a specific load) was measured according to ASTM D-648-72 with load of 18.5 kg/cm$^2$ and heating rate 2° C./min; MFI (melt flow index) was determined according to ASTM D1238. The compositions tested and the results are set out in Table 4.

TABLE 4

| | Example | | |
|---|---|---|---|
| | 8 | 9 | 10 |
| FR | Product of Example 1 | Product of Example 7 | FR 803P |
| PA 66 (Aculon S 223-D) | 46.3 | 51.3 | 43.5 |
| GF ChopVantage 3660 | 30 | 30 | 30 |
| FR | 16.9 | 13.3 | 19.7 |
| AO M-0112 | 6.3 | 4.8 | 6.2 |
| Acrawax C | 0.2 | 0.2 | 0.2 |
| Irganox B1171 | 0.2 | 0.2 | 0.2 |
| Ca-stearate | 0.2 | 0.2 | 0.2 |
| Br (calculated) | 13 | 10 | 13 |
| Sb$_2$O$_3$ (calculated) | 4.8 | 3.7 | 4.8 |
| Br/Sb$_2$O$_3$ (calculated) | 2.7 | 2.7 | 2.7 |
| Total flaming time | 10 | 19 | 32 |
| Max. flaming time | 1 | 5 | 8 |
| No. of dripping | 0 | 5 | 0 |
| No. of cotton ignition | 0 | 0 | 0 |
| Rating | V-0 | V-0 | V-0 |
| Izod Impact | 104 | 103 | 111 |
| Tensile strength | 150 | 150 | 143 |
| Elongation at yield | 2.6 | 3.3 | 3 |
| Elongation at break | 4.2 | 4.7 | 3.3 |
| Tensile modulus | 10747 | 9948 | 10044 |
| MFI | 11 | 29 | 7 |
| HDT | 226 | 231 | 225 |

Examples 11-13

V-2 and V-0 Rated Flame Retarded Formulations of Polypropylene Impact Copolymers The product of Example 7, pentakis(pentabromobenzyl) diphenylethane, was tested in compositions of polypropylene impact copolymers according to the procedure described below.

Ingredients Used to Prepare the Compositions

The materials used for preparing the polypropylene compositions are tabulated in Table 5:

TABLE 5

| Component (manufacturer) | GENERAL DESCRIPTION | FUNCTION |
|---|---|---|
| PP Capilene SL-50 (Caol) | polypropylene impact copolymer | plastic matrix |
| Product of Example 7 | Pentakis(pentabromobenzyl) diphenylethane | flame retardant |
| FR00112 (Kafrit) | Antimony trioxide masterbatch which contains 80 wt % Sb$_2$O$_3$ | FR synergist |
| Lotalc | Talc | Filler |
| Irganox B 225 (Ciba) | Antioxidant/processing stabilizer Irganox 1010:Irgafos 168 1:1 blend | Antioxidant & heat stabilizer. |

Preparation of Compositions and Test Specimens

The ingredients were pre-mixed, and fed via volumetric feeder #2 to the port of a twin-screw co-rotating extruder ZE25 with L/D=32 from Berstorff. Specific conditions are presented in Table 6:

TABLE 6

| PARAMETER | UNITS | Set values |
|---|---|---|
| Screws | | Medium shear A |
| Feeding zone temperature ($T_1$) | °C. | no heating |
| $T_2$ | °C. | 160 |
| $T_3$ | °C. | 180 |
| $T_4$ | °C. | 200 |
| $T_5$ | °C. | 200 |
| $T_6$ | °C. | 210 |
| $T_7$ | °C. | 210 |
| $T_8$ | °C. | 220 |
| $T_9$ | °C. | 230 |
| Screw speed | RPM | 350 |
| Feeding rate | Kg/h | 15 |

The strands produced were pelletized in a pelletizer 750/3 from Accrapak Systems Ltd. The resultant pellets were dried in a circulating air oven at 80° C. for 3 hours. The dried pellets were injection molded into test specimens using Allrounder 500-150 from Arburg as tabulated Table in 7.

TABLE 7

| PARAMETER | UNITS | Set values |
|---|---|---|
| $T_1$ (Feeding zone) | °C. | 50 |
| $T_2$ | °C. | 220 |
| $T_3$ | °C. | 220 |
| $T_4$ | °C. | 220 |
| $T_5$ (nozzle) | °C. | 230 |
| Mold temperature | °C. | 40 |
| Injection pressure | bar | 600 |
| Holding pressure | bar | 450 |
| Back pressure | bar | 60 |
| Holding time | sec | 5 |
| Cooling time | sec | 18 |
| Mold closing force | kN | 500 |

TABLE 7-continued

| PARAMETER | UNITS | Set values |
|---|---|---|
| Filling volume (portion) | ccm | 38 |
| Injection speed | ccm/sec | 30 |

The specimens were conditioned for one week at 23° C., and were then subjected to the tests outlined below.

Tests

Flammability Test

The flammability test was carried out according to the Underwriters-Laboratories standard UL 94, applying the vertical burn on specimens of 1.6 mm thickness.

Mechanical Properties

Impact strength was measured using the Izod notched test according to ASTM D-256-81, using pendulum impact tester type 5102 (Zwick); Tensile properties (tensile strength, tensile modulus, elongation at break) were measured in Zwick/Roell Z010 material testing machine according to ASTM D-638-95 (v=5, test speed 10 mm/min).

Thermal Properties

HDT (heat distortion temperature; this is the temperature at which a polymer sample deforms under a specific load) was measured according to ASTM D-648-72 with load of 1820 kPa and heating rate of 120° C./hour; the instrument is HDT/Viact-plus from Davenport, Lloyd instruments. MFI (melt flow index) was determined according to ASTM D1238 (230° C./2.16 kg); the instrument is Meltflixer 2000 from Thermo Hake. The compositions tested and the results are set out in Table 8.

TABLE 8

| | Example | | |
|---|---|---|---|
| | 10 | 11 | 12 |
| Composition (by weight %): | | | |
| Polypropylene impact copolymer | 56.7 | 55.1 | 53.3 |
| FR of Example 7 | 29.3 | 22.7 | 24.0 |
| Lotalc 25 | | 15.0 | 15.0 |
| Antimony trioxide masterbatch | 13.8 | 7.1 | 7.5 |
| Irganox B 225 | 0.2 | 0.2 | 0.2 |
| Bromine content, % calculated | 22.0 | 17.0 | 18.0 |
| Antimony trioxide, % calculated | 11.0 | 5.7 | 6.0 |
| Bromine/Sb$_2$O$_3$ ratio | 2.0 | 3.0 | 3.0 |
| Properties | | | |
| Flammability test: | | | |
| UL-94 vertical burning test at 1.6 mm thickness | | | |
| Maximal flaming time (sec) | 6 | 10 | 6 |
| Total Flaming time (sec) | 16 | 42 | 28 |
| Number of Specimens dripped | 5 | 5 | 5 |
| Number of cotton ignition | 0 | 1 | 0 |
| Rating | V-0 | V-2 | V-0 |
| Mechanical Properties | | | |
| Impact strength (J/m) | 27 | nd | 28 |
| Tensile strength (N/mm2) | 17.2 | nd | 18 |
| Elongation at break (%) | 64 | nd | 27 |
| Tensile modulus (N/mm2) | 1490 | nd | 2060 |
| Thermal properties | | | |
| HDT (° C.) | 63 | nd | 67 |
| MFI (g/10 min) | 4.1 | nd | 3.5 |

Example 14

V-0 Rated Flame Retarded Formulation of ABS

The product of Example 7, pentakis(pentabromobenzyl) diphenylethane, was tested in compositions of ABS according to the procedure described below.

Ingredients Used to Prepare the Compositions

The materials used for preparing the ABS compositions are tabulated in Table 9:

TABLE 9

| Component (manufacturer) | GENERAL DESCRIPTION | FUNCTION |
|---|---|---|
| ABS Magnum 3404 (Styron) | Acrylonitrile-butadiene-styrene copolymer | plastic matrix |
| Product of Example 7 | Pentakis(pentabromobenzyl) diphenylethane | flame retardant |
| FR00112 (Kafrit) | Antimony trioxide masterbatch which contains 80 wt % Sb$_2$O$_3$ | FR synergist |
| Hostaflon 2017 (Dyneon) | PTFE | Anti-dripping agent |
| Irganox B 225 (Ciba) | Phenol:Phosphite 3:1 based stabilizer | Antioxidant & heat stabilizer. |

Preparation of Compositions and Test Specimens

The compounding was performed in a twin-screw co-rotating extruder ZE25 with L/D=32 from Berstorff. Specific conditions are presented in Table 10.

TABLE 10

| PARAMETER | UNITS | Set values |
|---|---|---|
| Screws | | Medium shear A |
| Feeding zone temperature (T$_1$) | ° C. | no heating |
| T$_2$ | ° C. | 180 |
| T$_3$ | ° C. | 200 |
| T$_4$ | ° C. | 210 |
| T$_5$ | ° C. | 210 |
| T$_6$ | ° C. | 210 |
| T$_7$ | ° C. | 220 |
| T$_8$ | ° C. | 230 |
| T$_9$ | ° C. | 240 |
| Screw speed | RPM | 350 |
| Feeding rate | Kg/h | 15 |

The strands produced were pelletized in a pelletizer 750/3 from Accrapak Systems Ltd. The resultant pellets were dried in a circulating air oven at 80° C. for 3 hours. The dried pellets were injection molded into test specimens using Allrounder 500-150 from Arburg as tabulated in Table 11.

TABLE 11

| PARAMETER | UNITS | Set values |
|---|---|---|
| T$_1$ (Feeding zone) | ° C. | 210 |
| T$_2$ | ° C. | 215 |
| T$_3$ | ° C. | 220 |
| T$_4$ | ° C. | 230 |
| T$_5$ (nozzle) | ° C. | 230 |
| Mold temperature | ° C. | 40 |
| Injection pressure | bar | 900 |
| Holding pressure | bar | 800 |
| Back pressure | bar | 50 |
| Holding time | sec | 7 |
| Cooling time | sec | 10 |
| Mold closing force | kN | 500 |
| Filling volume (portion) | ccm | 38 |
| Injection speed | ccm/sec | 25 |

The specimens were conditioned for one week at 23° C., and were then subjected to the tests outlined below.

Tests

Flammability Test

The flammability test was carried out according to the Underwriters-Laboratories standard UL 94, applying the vertical burn on specimens of 1.6 mm thickness.

Mechanical Properties

Impact strength was measured using the Izod notched test according to ASTM D-256-81; Tensile properties (tensile strength, tensile modulus, elongation at break) were measured in Zwick/Roell Z010 material testing machine according to ASTM D-638-95 (v=50 mm/min).

Thermal Properties

HDT was measured according to ASTM D-648-72 with load of 1820 kPa and heating rate of 120° C./hour; the instrument is HDT/Vicat-plus from Davenport, Lloyd instruments. MFI (melt flow index) was determined according to ASTM D1238 (200° C./5 kg); the instrument is Meltflixer 2000 from Thermo Hake. The compositions tested and the results are set out in Table 12.

TABLE 12

|  | Example 14 |
|---|---|
| Composition (by weight %): | |
| ABS | 80.4 |
| FR of Example 7 | 17.4 |
| Antimony trioxide masterbatch | 1.9 |
| PTFE | 0.1 |
| Irganox B 225 | 0.2 |
| Bromine content, % calculated | 13.0 |
| Antimony trioxide, % calculated | 1.5 |
| Bromine/Sb$_2$O$_3$ ratio | 8.66 |
| Properties | |
| Flammability test: | |
| UL-94 vertical burning test at 1.6 mm thickness | |
| Maximal flaming time (sec) | 9 |
| Total Flaming time (sec) | 24 |
| Max glowing time | 0 |
| Number of specimens which dripped | 0 |
| Number of cotton ignition | 0 |
| Number of specimen burned up to the clamp | 0 |
| Rating | V-0 |
| Mechanical Properties | |
| Impact strength (J/m) | 104 |
| Tensile strength (N/mm2) | 39 |
| Elongation at break (%) | 13 |
| Tensile modulus (N/mm2) | 2161 |
| Thermal properties | |
| HDT (° C.) | 78 |
| MFI (g/10 min) | 11.7 |

The invention claimed is:

1. A process for preparing a compound of the formula Ar(—CH$_2$C$_6$Br$_5$)$_y$, wherein Ar indicates a structure comprising one or more six-membered aromatic ring(s), —CH$_2$C$_6$Br$_5$ is the pentabromobenzyl group and y indicates the number of the —CH$_2$C$_6$Br$_5$ groups in the compound, said process comprises a Friedel-Crafts alkylation reaction of pentabromobenzyl halide with a reactant, wherein said reactant contains one or more six-membered aromatic rings, in the presence of a Friedel-Crafts catalyst, to form said Ar(CH$_2$C$_6$Br$_5$)$_y$ compound having not less than two —CH$_2$C$_6$Br$_5$ groups bonded to each said one or more six-membered aromatic rings, such that the bond is between a carbon atom of the six-membered aromatic ring and the benzylic carbon of the pentabromobenzyl group.

2. A process according to claim 1, wherein three —CH$_2$C$_6$Br$_5$ groups are attached to each six-membered aromatic rings present in the reactant.

3. A process according to claim 1, wherein the Friedel-Crafts catalyst is selected from the group consisting of AlCl$_3$, AlBr$_3$, GaCl$_3$, FeCl$_3$, SnCl$_4$, SbCl$_3$, ZnCl$_2$, CuCl$_2$ and HF.

4. A process according to claim 1, wherein the reactant is a compound of Formula (II):

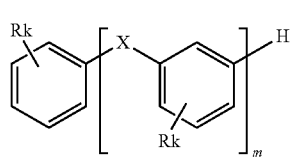

wherein R is H or a linear or branched aliphatic chain, m is 0 or 1, k is an integer from 1 to 3, X=null, an alkylene group containing 1 to 10 carbon atoms, O and S.

5. A process according to claim 4, wherein the reactant is selected from the group consisting of:
Toluene, wherein in Formula II m=0, R=CH$_3$, k=1;
Xylene, wherein in Formula II m=0, R=CH$_3$, k=2;
Ethylbenzene, wherein in Formula II m=0, R=C$_2$H$_5$, k=1;
Diphenyl ether, wherein in Formula II m=1, R=H, X=O;
Diphenylmethane, wherein in Formula II m=1, R=H, X=—CH$_2$—; and
Diphenylethane, wherein in Formula II m=1, R=H, X=—(CH$_2$)$_2$—.

6. A process according to claim 5, comprising a Friedel-Crafts alkylation reaction of pentabromobenzyl bromide with a reactant selected from the group consisting of toluene, xylene, ethylbenzene, diphenyl ether, diphenylmethane and diphenylethane in the presence of aluminum chloride, wherein the molar ratio between said pentabromobenzyl bromide and said reactant is at least equal to twice the number of the six-membered aromatic rings of said reactant.

7. A process according to claim 1, wherein the Friedel-Crafts alkylation reaction takes place in a solvent which is halogenated aliphatic hydrocarbon.

8. A product mixture consisting of homologous series of the formula Ar(—CH$_2$C$_6$Br$_5$)$_y$, where Ar indicates a structure comprising one or more six-membered aromatic ring(s) and —CH$_2$C$_6$Br$_5$ indicates a pentabromobenzyl group, wherein the benzylic carbon of said —CH$_2$C$_6$Br$_5$ group is bonded to a carbon atom of said six-membered aromatic ring(s), and further wherein said homologous series comprises the compound Ar(—CH$_2$C$_6$Br$_5$)$_{3m+3}$, where m+1 is the number of the six-membered aromatic rings in Ar.

* * * * *